US012097233B1

(12) United States Patent
Rahman

(10) Patent No.: US 12,097,233 B1
(45) Date of Patent: Sep. 24, 2024

(54) COMPOSITION FOR TREATING NIGHT BLINDNESS

(71) Applicant: KING FAISAL UNIVERSITY, Al-Ahsa (SA)

(72) Inventor: Aminur Rahman, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/545,896

(22) Filed: Dec. 19, 2023

(51) Int. Cl.
*A61K 36/42* (2006.01)
*A61K 9/00* (2006.01)
*A61K 35/407* (2015.01)
*A61P 27/02* (2006.01)

(52) U.S. Cl.
CPC ............ *A61K 36/42* (2013.01); *A61K 9/0056* (2013.01); *A61K 35/407* (2013.01); *A61P 27/02* (2018.01)

(58) Field of Classification Search
CPC .... A61K 36/42; A61K 9/0056; A61K 35/407; A61P 27/02
See application file for complete search history.

(56) References Cited

PUBLICATIONS

Quan et al. (CN109393350A Translation) (Year: 2019).*
Harine Sargunam ("Ivy gourd—medicinal and nutritional values". Int J Curr Res. 2017; 9(03): 47604-47607) (Year: 2017).*
John E. Dowling and George Wald Vitamin A Deficiency And Night Blindness Biological Laboratories of Harvard University, Cambridge, Communicated May 16, 1958.
M Umamaheswari and T K Chatterjee In Vitro Antioxidant Activities of the Fractions of *Coccinia grandis* L. Leaf Extract, PMID: 20162057; PMCID: PMC2816591.
Packirisamy Meenatchi, Ayyakkanuu Purushothaman and Sivaprakasam Maneemegalai Antioxidant, antiglycation and insulinotrophic properties of *Coccinia grandis* (L.) in vitro: Possible role in prevention of diabetic complications, DOI: 10.1016/j.jtcme.2016.01.002.
Pekamwar S. S, Kalyankar T.M., and Kokate S.S Pharmacological Activities of *Coccinia grandis*: Review DOI: 10.7324/JAPS.2013. 3522.
Lindeboom G A Historical milestones in the treatment of night blindness PMID: 6085992.
Teshome, Z. et al., "Genetic diversity in anchote (*Coccinia abyssinica* (Lam.) Cogan) using microsatellite markers", Current Plant Biology 24 (2020) 100167.
Whitney and Rolfes, "The Trace Minerals" (2010).
Yadav, L, et al. , "Genetic diversity, morphological traits, quality traits and antioxidants potentiality of *Coccinia grandis* germplasm under rainfed semi-arid region", scientific reports (2024).
Boron, B., et al., "Effect of Zinc Deficiency on Hepatic Enzymes Regulating Vitamin A Status 1,2" , Nutrient Interactions (1988).
Christian, K, et al., "Interactions between Zinc and Vitamin A: An update" , American Journal of Clinical Nutrition (1998).
Christian P, et al., "Zinc supplementation might potentiate the effect of vitamin A in restoring night vision in pregnant Nepalese women1-3" (2001).

* cited by examiner

*Primary Examiner* — Robert A Wax
*Assistant Examiner* — Quanglong N Truong
(74) *Attorney, Agent, or Firm* — Nath, Goldberg & Meyer; Joshua B. Goldberg

(57) ABSTRACT

A composition for treating night blindness includes *Coccinia grandis* (L.) stem and goat liver for the treatment of night blindness. The composition is edible and demonstrates remarkable therapeutic results when administered to a patient suffering from night blindness. In an embodiment, the composition can cure night blindness within 3 to 5 days of treatment.

8 Claims, No Drawings

COMPOSITION FOR TREATING NIGHT BLINDNESS

BACKGROUND

1. Field

The disclosure of the present patent application relates to a composition for treating night blindness and, particularly, to a composition for treating night blindness that includes *Coccinia grandis* and goat liver.

2. Description of the Related Art

Night blindness is described as the inability to see objects in low light conditions, which are recognizable under normal light environments. It is believed that a delay in the recycling of 11-cis-retinal is responsible for development of night blindness. Although retinoids can be administered to treat night blindness, chronic administration of conventional retinoid drugs can cause changes in lipid metabolism, damage to the liver, nausea, vomiting, blurred vision, damage to bones, interference with bone development and several other serious undesirable effects. It is therefore necessary to properly balance the need for improving visual function, while avoiding or minimizing adverse effects to provide appropriate benefit while reducing risk for the patient.

Thus, a non-toxic composition for treating night blindness solving the aforementioned problems is desired.

SUMMARY

The present subject matter relates to a composition for treating night blindness including *Coccinia grandis* (L.) stem and goat liver. The composition is edible and demonstrates remarkable therapeutic results when administered to a patient suffering from night blindness. In an embodiment, the composition can cure night blindness within 3 to 5 days of treatment.

In an embodiment, the present subject matter relates to a method of treating night blindness, comprising administering a therapeutically effective amount of a composition for treating night blindness including *Coccinia grandis* (L.) stem and goat liver. In an embodiment, the composition can be orally administered to the patient. In an embodiment, the composition can be administered to the patient for a period of time ranging from about 3 days to about 10 days.

According to an embodiment, a composition for treating night blindness can be prepared by extracting juice from the stems of *Coccinia grandis*, combining the extracted juice with cooked goat liver to form a mixture, and heating the mixture to provide the composition.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "patient" refers to any single subject for which treatment is desired. In certain embodiments, the patient herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The present subject matter relates to a composition for treating night blindness including a juice extracted from *Coccinia grandis* (L.) and goat liver for the treatment of night blindness. The composition is edible and demonstrates remarkable therapeutic results when administered to a patient suffering from night blindness. In an embodiment, the composition can cure night blindness within 3 to 5 days of treatment.

In an embodiment, the composition may be prepared by extracting the juice of the *Coccinia grandis* plant; combining the juice with cooked goat liver to provide a mixture; and heating the mixture for a period of time ranging from about 5 minutes to about 10 minutes. In an embodiment, the juice can be extracted from stems of the *Coccinia grandis* plant. In an embodiment, the juice can be extracted from twelve stems of the *Coccinia grandis* plant. In an embodiment, the stems of the *Coccinia grandis* plant can be bruised prior to heating. In an embodiment, the composition can be administered orally to a patient for treating night blindness.

In an embodiment one or more flavoring agents can be added to the mixture while the mixture is being heated. The one or more flavoring agents can be selected from the group consisting of salt, garlic, onion, ginger, pepper, cardamom, cinnamon, cumin, and combinations thereof. In one embodiment, oil is added to the mixture.

In an embodiment, the cooked goat liver is prepared by cooking about 150 grams to about 170 grams of raw goat liver for a period of time ranging from about 10 minutes to about 15 minutes at a temperature ranging from about 145° F. to about 160° F. In an embodiment, the goat liver is cooked for a period of time ranging from about 10 minutes to about 15 minutes at a temperature of about 145° F.

According to an embodiment a method of treating night blindness can include administering a composition including a juice extracted from *Coccinia grandis* (L.) and goat liver to a patient in need thereof. In an embodiment, the composition can be administered orally, once daily for a period of about 3 days to about 5 days.

It is believed that the composition has a high concentration of vitamin A. Vitamin A is essential for maintaining normal vision, particularly in low light conditions. As night blindness can occur when there is a deficiency of this vitamin, the present composition can improve symptoms of night blindness soon after the composition is administered to a patient suffering from this condition.

The present teachings are illustrated by the following examples.

Example 1

Preparing Extract Juice from *Coccinia grandis*

Young, fresh, and tender *Coccinia grandis* stems were chosen for extracting juice, as they have a higher juice content and a mild flavor. The *Coccinia grandis* stems were thoroughly rinsed under running water to remove any dirt or debris. The stems of *Coccinia grandis* were then dried with a clean cloth or paper towel. The stems of *Coccinia grandis* were cut into smaller pieces (approximately 2.5 cm) using a sharp scalpel. Twelve pieces of the stem were bruised with a mortar and pestle before heating. Then, the bruised pieces were transferred immediately to a pot.

Approximately 150 grams to 170 grams of goat liver were sliced and soaked in water. The water was removed, and the sliced liver was then cooked for about 10-15 minutes at medium heat or a temperature of at least 145° F. (63° C.). Various spices, including cooking oil, salt, garlic, onion, ginger, pepper, cardamom, cinnamon, and cumin, were added in small amounts to the liver during cooking. After 10 minutes of cooking, the bruised pieces of *Coccinia grandis* stems were combined with the liver and cooked for 5 to 10 minutes or until the liver was cooked through. The cooked composition was then administered to the patient immediately.

Example 2

Treatment with Composition Including Goat Liver and *Coccinia grandis*

The composition comprising approximately 150 grams to 170 grams of liver with the twelve stems of *Coccinia grandis*, was administered orally to patients during their regular evening meal. The composition was ingested once daily for a duration of 3 to 5 days. The recorded results are provided below.

A 53-year-old man, presented to a clinic with a chief complaint of night blindness, persisting for the last 2 months. The patient reported a gradual onset of difficulty seeing at night, with a significant impact on his daily activities. He denied any history of trauma, systemic illness, or medication use that could explain his visual symptoms. His medical history was otherwise unremarkable, with no known ophthalmic conditions.

The patient was advised to incorporate the composition of liver and stems of *Coccinia grandis*, containing high concentrations of vitamin A. The patient followed the prescribed regimen, consuming the liver and stems of *Coccinia grandis* composition during dinner for a period of five days. After five days, the patient reported a remarkable improvement in his night vision. He stated that he could now see clearly in low light conditions and no longer experienced the previous difficulty navigating at night.

A 49-year-old woman presented to a clinic with a chief complaint of night blindness, persisting for the last 3 months. The patient reported a progressive inability to see in low-light conditions, particularly at night. She denied any history of ocular trauma, systemic illnesses, or medication use that might explain her visual symptoms. She described significant difficulty in navigating and recognizing objects in low-light environments.

The patient was advised to consume the composition of goat liver and stems of *Coccinia grandis*, for its high vitamin A content. The patient diligently followed the prescribed dietary regimen, consuming the liver and stems of *Coccinia grandis* composition during dinner for a period of five days. After five days, she reported a significant improvement in her night vision. She stated that she could now see more clearly in low light conditions and no longer experienced the previous difficulty at night.

An 11-year-old girl, presented to a clinic with a chief complaint of night blindness persisting for one month. Her parents reported that their daughter had been having trouble seeing in low light conditions, particularly at night. There was no history of trauma, systemic illnesses, or medication use.

The patient was advised to consume the composition of liver and stems of *Coccinia grandis*. The patient diligently followed the prescribed dietary regimen, consuming the liver and stems of *Coccinia grandis* composition during dinner for a period of three days. After three days, her parents reported a significant improvement in their daughter's night vision. She confirmed that she could see more clearly in low light conditions and no longer experienced the previous difficulty at night.

A 30-year-old man, presented to a clinic with a chief complaint of night blindness, persisting for the last three weeks. He reported a sudden onset of difficulty seeing in low-light conditions, particularly at night. There was no history of trauma, systemic illnesses, or recent medication use.

The patient was advised to consume a composition including goat liver and stems of *Coccinia grandis*. The patient diligently followed the prescribed dietary regimen, consuming the liver and stems of *Coccinia grandis* composition during dinner for a period of four days. After four days, he reported a significant improvement in his night vision. He confirmed that he could see more clearly in low light conditions and no longer experienced the previous difficulty at night.

It is to be understood that the compositions and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of preparing a composition for treating night blindness, the composition for treating night blindness comprising juice extracted from *Coccinia grandis* (L.) and goat liver, wherein the method comprises extracting the juice of the *Coccinia grandis* plant; combining the juice with cooked goat liver to provide a mixture; and heating the mixture for a period of time ranging from about 5 minutes to about 10 minutes at a temperature ranging from about 125° F. to about 155° F.

2. The method of claim 1, wherein the juice of the *Coccinia grandis* plant is extracted from the stem of the *Coccinia grandis* plant.

3. The method of claim 2, wherein the juice of the *Coccinia grandis* plant is extracted from twelve stems of the *Coccinia grandis* plant.

4. The method of claim 3, wherein the cooked goat liver is prepared by cooking about 150 grams to about 170 grams of raw goat liver for a period of time ranging from about 10 minutes to about 15 minutes at a temperature ranging from about 145° F. to about 160° F.

5. A method of treating night blindness, comprising orally administering a composition to a patient in need thereof, wherein the composition comprises:
juice extracted from *Coccinia grandis* (L.); and
goat liver.

6. The method of claim 5, wherein the composition is administered once daily for a period of about 3 days to about 5 days.

7. A method of treating night blindness, comprising administering to a patient in need thereof, a composition comprising:
juice extracted from *Coccinia grandis* (L.); and
goat liver.

8. The method of claim 7, wherein the composition is administered once daily for a period of 3 days to about 5 days.

* * * * *